(12) United States Patent
Nose et al.

(10) Patent No.: US 7,156,873 B2
(45) Date of Patent: Jan. 2, 2007

(54) METHODS FOR DETECTING AN ABNORMAL CONDITION OF A BLOOD PUMP SYSTEM

(75) Inventors: Yukihiko Nose, Houston, TX (US); Toshiyuki Shinohara, Kawasaki (JP); Kuniyoshi Watanabe, Houston, TX (US); Fumiyuki Ichihashi, Ibaraki (JP)

(73) Assignees: Miwatec Co., Ltd., Kawasaki (JP); Baylor College of Medicine, Houston, TX (US)

( * ) Notice: Subject to any disclaimer, the term of this patent is extended or adjusted under 35 U.S.C. 154(b) by 458 days.

(21) Appl. No.: 10/655,486

(22) Filed: Sep. 3, 2003

(65) Prior Publication Data
US 2004/0133061 A1 Jul. 8, 2004

Related U.S. Application Data

(60) Provisional application No. 60/409,923, filed on Sep. 10, 2002.

(51) Int. Cl.
*A61N 1/362* (2006.01)
*A61M 1/00* (2006.01)

(52) U.S. Cl. ............... 623/3.1; 600/16; 600/17; 417/43; 417/44.1; 417/44.11; 417/63

(58) Field of Classification Search ............ 417/63, 417/43, 44.2, 44.11; 600/16–17; 623/3.1, 623/3.11; *A61N 1/362; A61M 1/00*
See application file for complete search history.

(56) References Cited

U.S. PATENT DOCUMENTS

| | | | | |
|---|---|---|---|---|
| 5,624,572 A | * | 4/1997 | Larson et al. | 210/746 |
| 6,176,822 B1 | * | 1/2001 | Nix et al. | 600/17 |
| 6,447,441 B1 | * | 9/2002 | Yu et al. | 600/16 |
| 6,554,577 B1 | * | 4/2003 | Park et al. | 417/44.1 |
| 6,866,625 B1 | * | 3/2005 | Ayre et al. | 600/16 |
| 6,954,713 B1 | * | 10/2005 | Eryurek | 702/140 |
| 2005/0004418 A1 | * | 1/2005 | Morello | 600/16 |

* cited by examiner

*Primary Examiner*—Robert E. Pezzuto
*Assistant Examiner*—Natasha Patel
(74) *Attorney, Agent, or Firm*—Lipsitz & McAllister, LLC

(57) ABSTRACT

The present invention provides methods for detecting an abnormal condition of a blood pump system based on the power consumption of the pump actuator. By plotting differentiated power consumption of the pump actuator over time against the power consumption, a plot pattern is obtained. A change of the plot pattern area and/or a movement of the plot pattern will indicate a change in condition of the pump. A Heart Pump Area (HPA) index may be established which corresponds to the changing area of the plot pattern over time. A Heart Pump Position (HPP) index may be established which corresponds to the changing position of the plot pattern over time (e.g., corresponding to the distance the plot pattern has moved). By plotting the HPA index against the HPP index, changes in the condition of the pump can be monitored and any abnormal condition of the pump can be detected.

12 Claims, 3 Drawing Sheets

METHODS FOR DETECTING AN ABNORMAL CONDITION OF A BLOOD PUMP SYSTEM

This application claims the benefit of U.S. provisional patent application No. 60/409,923 filed on Sep. 10, 2002, which is incorporated herein and made a part hereof by reference.

BACKGROUND OF THE INVENTION

The present invention relates to the control of rotary blood pumps for assisting a failing human heart. More specifically, the present invention relates to the detection of an abnormal condition of an implantable blood pump.

Various types of rotary blood pumps have been developed and are currently under development for use as heart assist devices. Compared to pulsatile pumps, rotary blood pumps have several advantages, including smaller size, higher efficiency, and a simpler design.

However, a servo control system for such rotary blood pumps has yet to be developed. Typically, operators have had to monitor patients in the intensive care unit in order to observe the condition of the pump and the patient, as manual intervention is currently required for controlling the rotational speed of the pump.

If such a rotary blood pump is to be used as a left ventricular assist device (LVAS), the pump flow should be increased when the pressurehead is decreased with the fixed rotational speed of the pump, because these parameters automatically adjust to the patient's physiological condition, regardless of the fixed rotational speed of the pump impeller. However, when the venous return suddenly becomes too low because of physiological changes or overpumping, a high negative pressure may result at the inlet port of the pump, which may lead to a suction condition within the atrium and veins, which may result in serious injury or even death.

In prior art systems, pump flow is typically measured by a flow meter and the position of the impeller of the pump is measured by an ultrasonic sensor.

It would be advantageous to detect an abnormal condition of the pump system without the need for a flow meter or other sensors. It would be advantageous to detect an abnormal condition of the pump system that is derived from power consumption of the pump actuator.

The methods of the present invention provide the foregoing and other advantages.

SUMMARY OF THE INVENTION

The present invention relates to the detection of an abnormal condition of an implantable blood pump without the need for flow meters or other sensors.

The present invention provides methods for detecting an abnormal condition of a blood pump system based on the power consumption of the pump actuator. There is a relationship between the power consumption of the pump actuator and the condition of the pump system. Rapid changes in the pump system may be detected by monitoring differentiated power consumption of the pump actuator over time.

By plotting differentiated power consumption of the pump actuator over time against the power consumption, a plot pattern may be obtained. The condition of the pump system may then be related to the area of the plot pattern and/or the position of the plot pattern. An abnormal condition will result in a change of the plot pattern area and/or a change in position of the plot pattern. For example, a reduction in the flow rate of the pump system may result in a reduced area of the plot pattern and a shift in position of the plot pattern.

The changing area of the plot pattern (represented by a Heart Pump Area (HPA) index) can be plotted against the movement of the plot pattern (represented by a Heart Pump Position (HPP) index) to provide a means for detecting any change in the normal condition of the pump system. An abnormal condition may include a suction condition, an overpumping condition, or an underpumping condition.

BRIEF DESCRIPTION OF THE DRAWINGS

The present invention will hereinafter be described in conjunction with the appended drawing figures, wherein like numerals denote like elements, and.

DETAILED DESCRIPTION OF THE INVENTION

The ensuing detailed description provides preferred exemplary embodiments only, and is not intended to limit the scope, applicability, or configuration of the invention. Rather, the ensuing detailed description of the preferred exemplary embodiments will provide those skilled in the art with an enabling description for implementing a preferred embodiment of the invention. It should be understood that various changes may be made in the function and arrangement of elements without departing from the spirit and scope of the invention as set forth in the appended claims.

The present invention takes advantage of the relationship between the power consumption of the pump actuator and the condition of the pump system in order to detect an abnormal condition of the pump system.

Figure 1A:
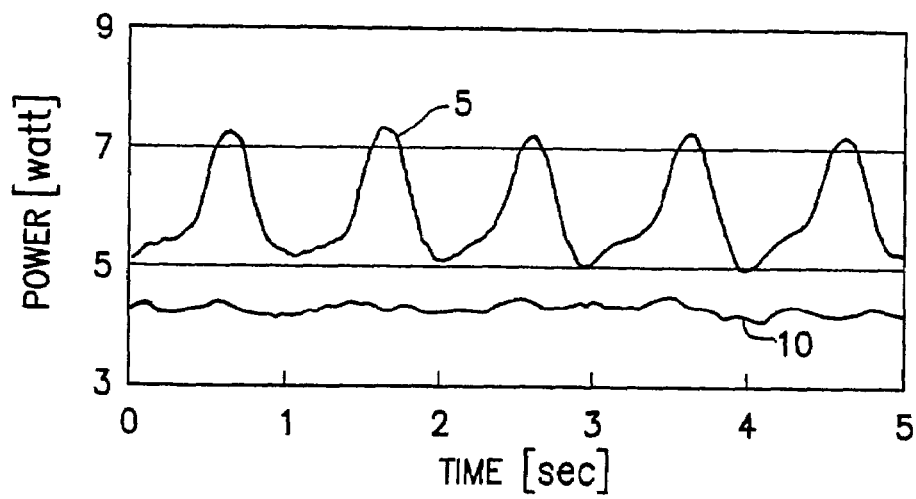
FIG. 1 (FIGS. 1A, 1B and 1C) illustrates the formation of the plot pattern used to detect the abnormal condition of the pump system in accordance with an example embodiment of the invention.
Figure 1B:
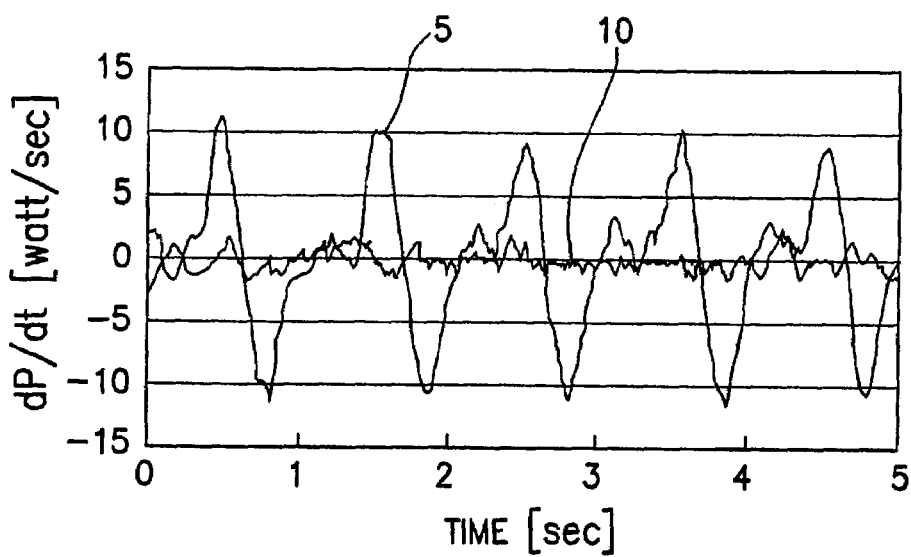
Figure 1C:
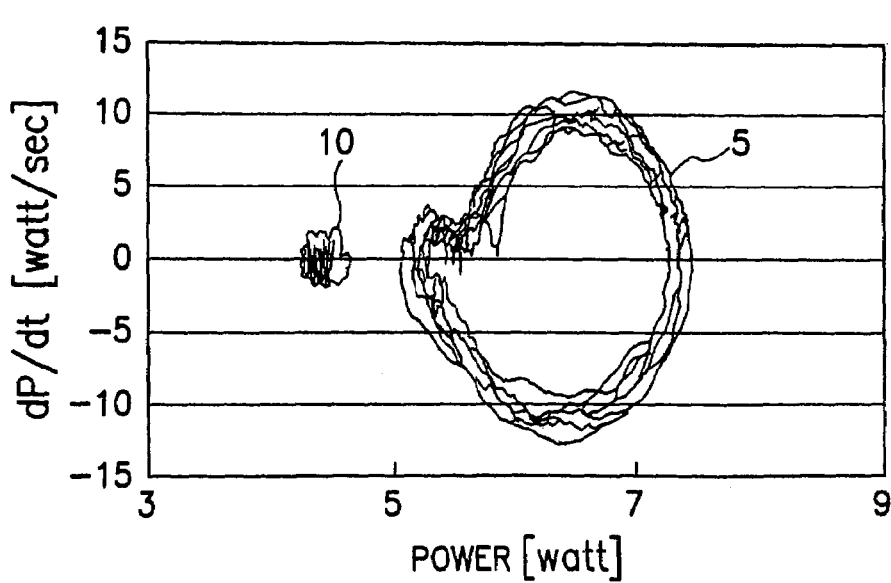

An example embodiment of the inventive method is shown in FIGS. 1A–1C. With the present invention, rapid changes in the pump system may be detected by monitoring differentiated power consumption of the pump actuator over time. FIG. 1A shows a plot of the power consumption of the pump actuator over time. FIG. 1B shows a plot of differentiated power consumption of the pump actuator over time. In an example embodiment of the invention, differentiated power consumption over time (FIG. 1B) may be plotted against the power consumption (FIG. 1A) to provide a plot pattern as shown in FIG. 1C. The condition of the pump system is related to the area of the plot pattern and the position of the plot pattern. Therefore, a change in the area and/or position of the plot pattern indicates a change in condition of the pump system. FIGS. 1A–1C show plots for both a normal pump condition 5 and an abnormal pump condition 10.

Figure 2:
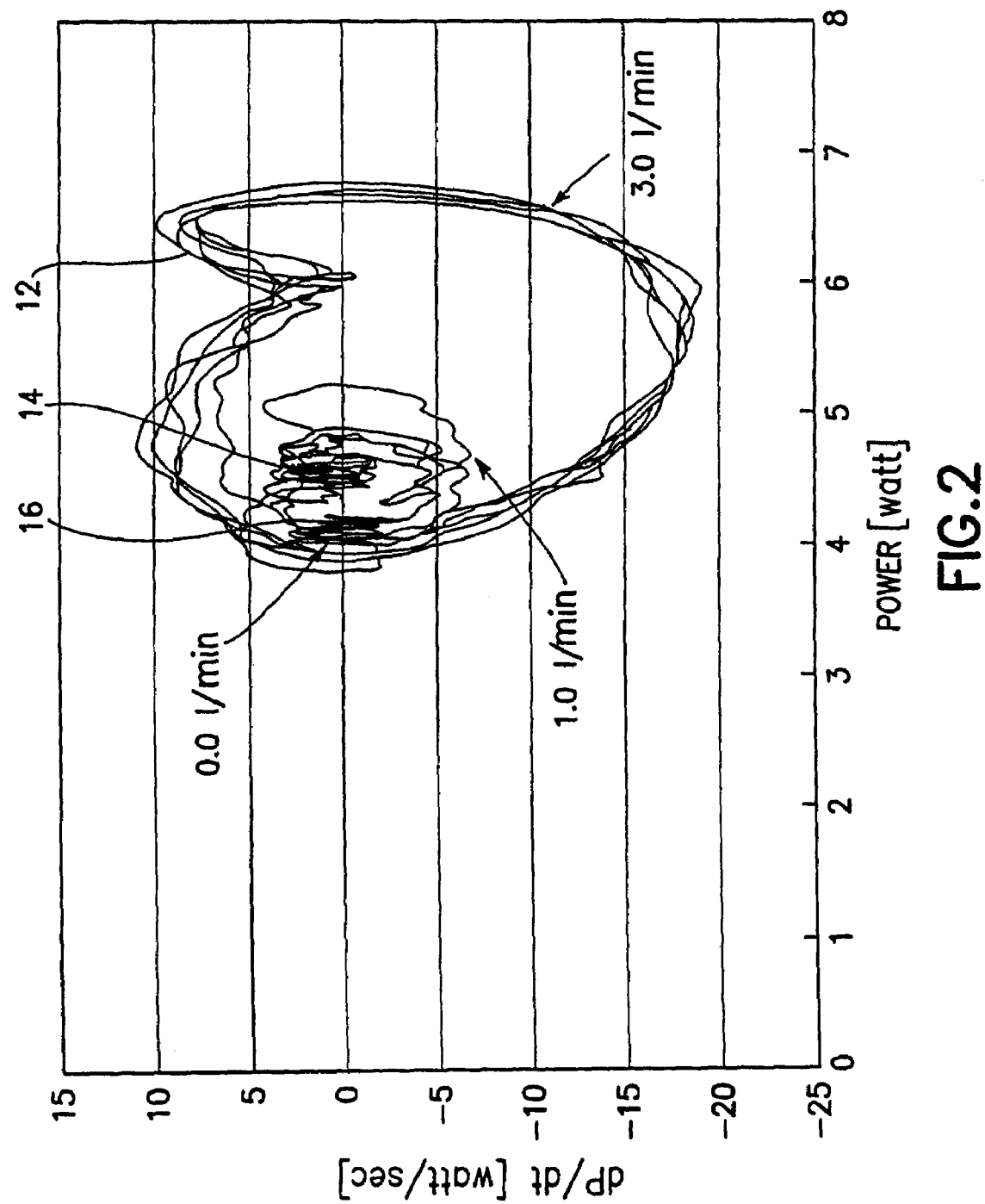
FIG. 2 shows the change in the plot pattern in response to a change in flow rate during restriction of pump inflow in accordance with an example embodiment of the invention.

For example, as shown in FIG. 2, when the flow rate is changed (e.g., by clamping the inflow graft in an in vivo study) an abnormal condition develops. This abnormal condition may be indicated by a change in area of the plot pattern and a change in position of the plot pattern. FIG. 2 shows that as the flow rate is decreased, the area of the resulting plot pattern is reduced and is shifted toward the left of the plot. In the example shown in FIG. 2, a normal flow rate of, for example, approximately 3.0 liters per minute results in plot pattern 12. When the flow rate is reduced to approximately 1.0 liter per minute, the plot pattern is shifted to the left and has a reduced area, as shown by plot pattern 14. A further reduction in the flow rate to approximately 0.1 liters per minute results in a further shift of the plot pattern to the left and a further reduction in the area of the plot pattern, as shown by plot pattern 16.

A Heart Pump Area (HPA) index may be established which corresponds to the changing area of the plot pattern over time. A Heart Pump Position (HPP) index may be established which corresponds to the changing position of the plot pattern over time (e.g., corresponding to the distance the plot pattern has moved). For example, a normal condition may be indicated by an HPA of 1.0 and an HPP of 1.0. An increase in the area of the plot pattern will result in an increased HPA index (e.g., an HPA of 1.2), and vice versa. A shift to the left of the plot pattern will result in a decrease of the HPP (e.g., an HPP of 0.8), and vice versa.

Figure 3:
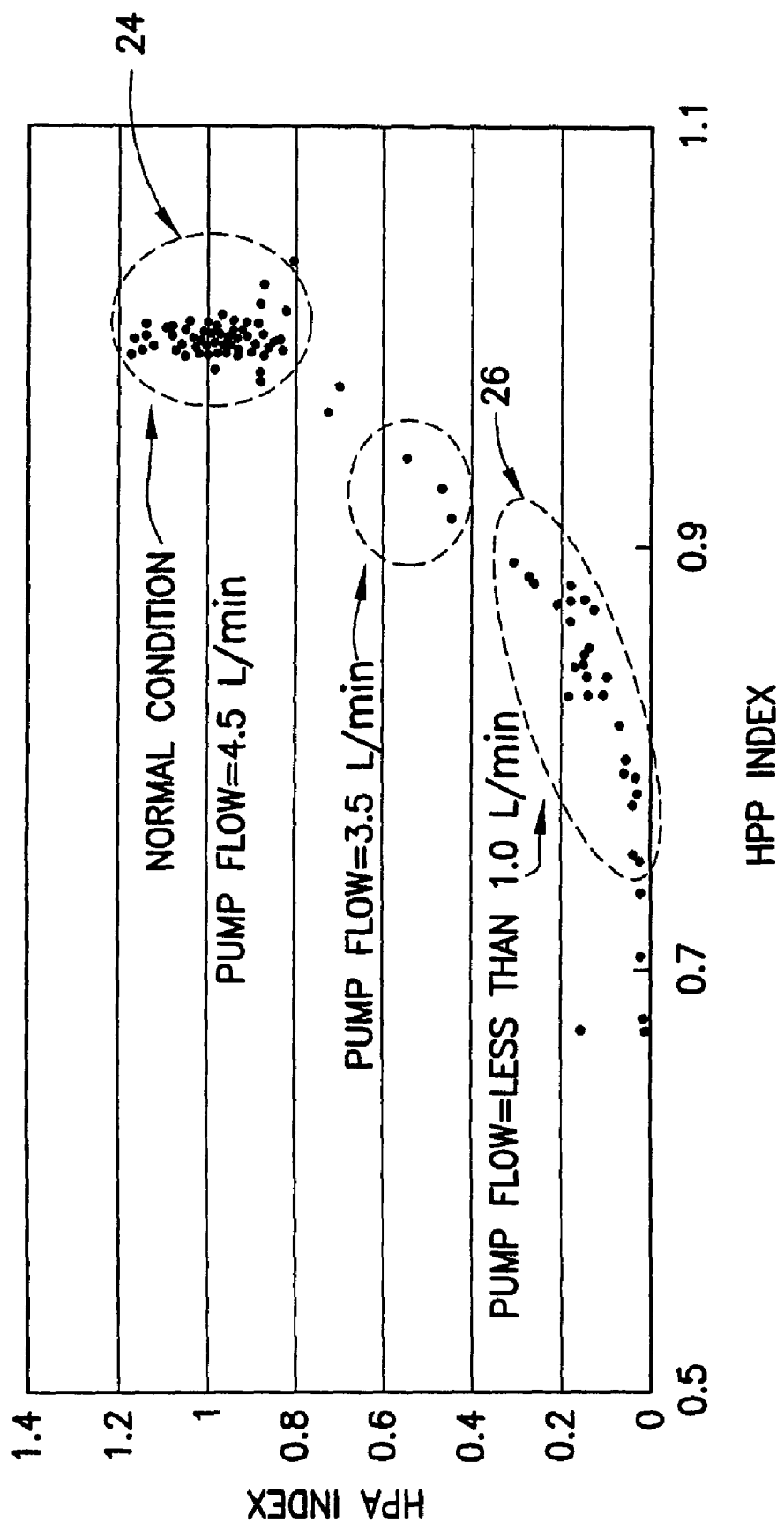
FIG. 3 shows a plot of the HPA index against the HPP index in accordance with an example embodiment of the invention.

As shown in FIG. 3, by plotting the HPA index against the HPP index, the condition of the pump can be determined. In the example shown in FIG. 3, a normal flow rate of 4.5 liters per minute is established, resulting in a normal condition 24. An abnormal condition 26 is detected when the flow rate is reduced to below 3.5 liters per minute. In this manner, an abnormal condition of the pump system can be detected without the need for a flow meter or other sensor.

Once the abnormal condition is detected, the pump system can then be controlled to restore the normal condition.

The abnormal condition may be a suction condition, an overpumping condition, or a underpumping condition. The suction condition may be indicated an increase in magnitude of the HPA and the HPP. The overpumping condition may be indicated by an increase in magnitude of the HPA and the HPP. The underpumping condition may be indicated by a decrease in the magnitude of the HPA and the HPP.

It should now be appreciated that the present invention provides advantageous methods for accurately detecting the condition of a pump system in a cost-effective manner without the need for flow meters or sensors.

Although the invention has been described in connection with various illustrated embodiments, numerous modifications and adaptations may be made thereto without departing from the spirit and scope of the invention as set forth in the claims.

What is claimed is:

1. A method for detecting an abnormal condition of an implantable blood pump system, comprising:
    monitoring differentiated power consumption of a pump actuator of the blood pump system; and
    plotting differentiated power consumption of the pump actuator over time against the power consumption of the pump actuator to provide a plot pattern;
    wherein a change in the plot pattern over time indicates a change in condition of the pump system.

2. A method in accordance with claim 1, wherein said change in the plot pattern comprises at least one of a change in area or position of said plot pattern.

3. A method for detecting an abnormal condition of an implantable blood pump system, comprising:
    monitoring differentiated power consumption of a pump actuator of the blood pump system; and
    plotting differentiated power consumption of the pump actuator over time against the power consumption of the pump actuator to provide a plot pattern;
    monitoring the plot pattern over time;
    wherein a reduced area of said plot pattern over time indicates a reduced flow rate of said pump system.

4. A method in accordance with claim 2, wherein a reduced area and a shift of said plot pattern indicates a reduced flow rate of said pump system.

5. A method for detecting an abnormal condition of an implantable blood pump system, comprising:
    monitoring differentiated power consumption of a pump actuator of the blood pump system;
    plotting differentiated power consumption of the pump actuator over time against the power consumption of the pump actuator to provide a plot pattern;
    establishing a Heart Pump Area (HPA) index corresponding to a changing area of the plot pattern over time;
    establishing a Heart Pump Position (HPP) index corresponding to a changing position of the plot pattern over time;
    plotting the HPA index against the HPP index; and
    detecting an abnormal condition of the pump system by monitoring changes in said plot of the HPA index against the HPP index over time.

6. A method in accordance with claim 5, further comprising:
    controlling said pump system in response to said detection of said abnormal condition.

7. A method in accordance with claim 5, wherein said abnormal condition comprises one of a suction condition, an overpumping condition, or an underpumping condition.

8. A method in accordance with claim 7, wherein:
    said suction condition is indicated by an increase in magnitude of said HPA and said HPP;
    said overpumping condition is indicated by an increase in magnitude of said HPA and said HPP; and
    said underpumping condition is indicated by a decrease in the magnitude of said HPA and said HPP.

9. A method in accordance with claim 1, wherein:
    said method is a probeless method.

10. A method in accordance with claim 1, wherein:
    said change in condition of said pump system is detected without the use of a flow sensor.

11. A method in accordance with claim 5, wherein:
    said method is a probeless method.

12. A method in accordance with claim 5, wherein:
    said abnormal condition is detected without the use of a flow sensor.

* * * * *